United States Patent [19]

Bryant et al.

[11] Patent Number: 5,063,234
[45] Date of Patent: Nov. 5, 1991

[54] METHOD OF INHIBITING DEMINERALIZATION OF BONE

[75] Inventors: Henry U. Bryant; James A. Clemens, both of Indianapolis, Ind.

[73] Assignee: Eli Lilly and Company, Indianapolis, Ind.

[21] Appl. No.: 684,524

[22] Filed: Apr. 11, 1991

Related U.S. Application Data

[63] Continuation-in-part of Ser. No. 529,031, May 25, 1990, abandoned.

[51] Int. Cl.$^5$ .................. A61K 31/48; A61K 31/415; C07D 457/02
[52] U.S. Cl. .................................. 514/288; 514/287; 546/64; 546/67
[58] Field of Search .................. 514/287, 288; 546/64, 546/67

[56] References Cited

U.S. PATENT DOCUMENTS

| | | | |
|---|---|---|---|
| 4,166,182 | 8/1979 | Kornfeld et al. | 546/67 |
| 4,201,881 | 5/1980 | DeLuca et al. | 568/819 |
| 4,202,979 | 5/1980 | Kornfeld et al. | 546/67 |
| 4,448,721 | 5/1984 | DeLuca et al. | 260/239.5 |
| 4,468,401 | 8/1974 | Hahn | 424/25 S |
| 4,675,322 | 6/1987 | Laguzza | 514/288 |

OTHER PUBLICATIONS

"Osteoporosis", vol. 5, No. 3, National Institutes of Health Consensus Development Statement.
Raisz, L., *Journal of the American Geriatrics Society*, 30, 127-138 (1982).
Krieger et al., *Calcif Tissue Int.*, 34, 239-244 (1982).
Schwartz et al., *Clin. Orthop.*, No. 192, 180-184 (1985).
Kalu et al., *Endocrinology*, 122, 1847-1854 (1988).

Primary Examiner—Richard L. Raymond
Assistant Examiner—S. Mark Clardy
Attorney, Agent, or Firm—John C. Demeter; Leroy Whitaker

[57] ABSTRACT

A method of inhibiting bone demineralization comprising administration of an effective amount of a compound having the formula

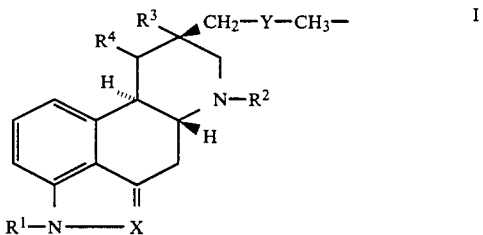

where
X is CH or N;
Y is O or S;
$R^1$ is 2-propenyl, $C_1$-$C_3$ alkyl, benzyl or substituted benzyl where the substitutents are one or two of the same or different and are selected from methyl, ethyl, methoxy, ethoxy, hydroxy, chloro, bromo, or fluoro;
$R^2$ is $C_2$-$C_3$ alkyl, allyl or cyclopropylmethyl;
$R^3$ and $R^4$ are both hydrogen or combine to form a carbon-carbon bond; and pharmaceutically acceptable acid addition salts thereof to a mammal requiring bone demineralization inhibition.

7 Claims, No Drawings

METHOD OF INHIBITING DEMINERALIZATION OF BONE

This application is a continuation-in-part of application Ser. No. 07/529,031 filed May 25, 1990, now abandoned.

The present invention relates to the use of certain ergoline analogues to inhibit bone demineralization.

BACKGROUND OF THE INVENTION

Mammalian bones serve two different and at times incompatible functions. Bones must be strong, light, and be capable of repair and remodeling in response to changing stress. Bones also serve as a metabolic reservoir for most of the calcium and phosphorous in the body, along with substantial amounts of magnesium, sodium, and carbonate.

Bone is a highly specialized connective tissue with unique properties derived from its extensive matrix structure. A network of fibrous bundles composed of the protein collagen is presumed to provide the tension-resistant behavior of bone. In addition, other material including proteoglycans, noncollagenous proteins, lipids, and acidic proteins associated with a mineral compound consisting primarily of hydroxyapatite, $Ca_{10}(PO_4)_6(OH)_2$, are deposited in the extensive matrix architecture of bone. Bone tissue is continuously renewed and remodeled throughout the life of mammals.

The processes of bone formation and renewal are carried out by specialized cells. Osteogenesis is presumably carried out by the "osteoblasts" (bone-forming cells). Remodeling of bone is apparently brought about by an interplay between the activities of bone-resorbing cells called "osteoclasts" and the bone-forming osteoblasts. The bony skeleton is thus not only an architectural structure with a mechanical function but also is a living tissue capable of growth, modeling, remodeling and repair. Since these processes are carried out by specialized living cells, chemical (pharmaceutical/hormonal), physical and physiochemical alterations can affect the quality, quantity, and shaping of bone tissue.

As part of their storage function, bones provide calcium and phosphorous when the supply of these elements is deficient. The sodium, phosphorous, and carbonate are also released to buffer excess acid in the diet. These responses preempt the structural functions of growth and remodeling such that bone mass may decrease due to calcium or phosphorous deficiency or with chronic acidosis.

"Bone demineralization," includes loss of both mineral and protein matrix components, resulting in a reduction in bone mass without a reduction in bone volume. Such demineralization occurs in a wide range of subjects, including post-menopausal women, patients who are undergoing or have undergone long-term administration of corticosteroids, patients suffering from Cushing's syndrome, and in patients having gonadal dysgenesis. Unchecked, the bone demineralization process leads to osteoporosis, a condition characterized by decrease in bone mass (decreased density and enlargement of bone spaces) without a reduction in bone volume producing porosity and fragility. It is estimated that thirty-five percent of women over the age of 65 suffer from osteoporosis. One of the chief rationales for estrogen-replacement therapy in post-menopausal women is avoidance of, or at least slowing down, the bone demineralization process and the onset of osteoporosis. Calcium therapy has been advocated for treatment of osteoporosis, and some steroids related to vitamin D are alleged to reduce the rate of bone resorption. See U.S. Pat. Nos. 4,448,721 and 4,201,881.

The ergoline ring is a tetracycle having the following structure:

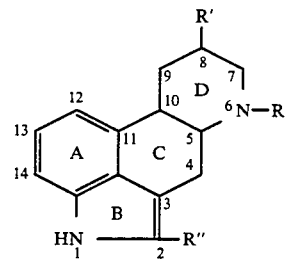

Certain substituted ergolines are known to be D-2 dopamine agonists having the ability to inhibit the secretion of prolactin and to affect favorably the symptoms of Parkinson's Syndrome. For example, in the foregoing structure when R is n-propyl, $R^1$ is methylthiomethyl, and R" is H, the substituted ergoline has been given the generic name pergolide, which is disclosed in U.S. Pat. No. 4,166,182. Pergolide has been proven to be effective in the treatment of some symptoms of Parkinsonism, and is being developed as the mesylate salt.

An object of this invention is to provide a novel therapeutic approach to the inhibition of bone demineralization and, by consequence, of osteoporosis, by administering certain ergoline compounds.

SUMMARY OF THE INVENTION

In fulfillment of the above and other objects, this invention provides a method of inhibiting bone demineralization, which comprises administering to a mammal in need of treatment, a bone demineralization inhibiting dose of a compound selected from: 8β-[(methoxy or methylthio)methyl]-8-ergolines and 8β-[(methoxy or methylthio)methyl]-8-ergolenes and their 2-aza analogues and pharmaceutically acceptable acid addition salts thereof.

DETAILED DESCRIPTION OF THE INVENTION

Ergot compounds are well known in the art and have been identified as possessing a number of pharmacological properties including inhibition of fertility, uterotonic activity, influence on body temperature, emetic activity, dopaminergic activity, inhibition of prolactin secretion and the like. Ergot compounds can be divided into four main structural groups: clavine alkaloids, lysergic acids, lysergic acid amides, and peptide alkaloids. See Berde and Schild, Eds. "Ergot Alkaloids and Related Compounds" Springer-Verlag, New York, 1978, pp. 1-61.

Pergolide is the generic name that has been given to the substituted ergoline D-6-n-propyl-8β-methylthiomethylergoline which is disclosed in U.S. Pat. No. 4,166,182, Example 1. U.S. Pat. No. 4,166,182 is incorporated by reference herein in its entirety. Pergolide has been proven to be effective in the treatment of some symptoms of Parkinsonism, and is being developed as the mesylate salt.

The method of treatment provided by this invention is practiced by administering to a mammal in need of bone demineralization inhibition a dose of a compound selected from 8β-[(methoxy or methylthio)methyl]ergolines and 8β-[(methoxy or methylthio)methyl]-8-ergolenes and 2-aza analogues of said ergolines and ergolenes and pharmaceutically acceptable acid addition salts thereof, that is effective to inhibit bone demineralization. The bone demineralization inhibition contemplated by the present method includes both medical therapeutic and/or prophylactic treatment, as appropriate. Generally, the compound is formulated with common excipients, diluents or carriers, and compressed into tablets, or formulated as elixirs or solutions for convenient oral administration. It can also be formulated for parenteral administration, for instance by the intramuscular or intravenous routes. The compounds can additionally be administered transdermally, and are well suited to formulation as sustained release dosage forms and the like.

Pharmaceutically acceptable acid addition salts of the compounds employed in this invention include salts derived from non-toxic inorganic acids such as: hydrochloric acid, nitric acid, phosphoric acid, sulfuric acid, hydrobromic acid, hydroiodic acid, and others, as well as salts derived from non-toxic organic acids such as aliphatic mono and dicarboxylic acids, phenyl-substituted alkanoic acids, hydroxyalkanoic and hydroxyalkandioic acid, aromatic acids, aliphatic and aromatic sulfonic acids. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benezenesulfonate, toluenesulfonate, chlorobenezenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate and mesylate. In addition, some of these salts may form solvates with water or organic solvents such as ethanol. These solvates are also included as compounds of this invention.

The compounds employed in the method of the present invention comprises 8β-[(methoxy or methylthio)methyl]ergolines or 8β-[(methoxy or methylthio)methyl]-8-ergolenes and their 2 aza derivatives having the formula

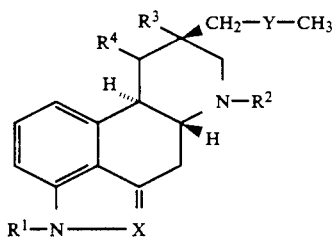

where
X is CH or N;
Y is O or S;
$R^1$ is 2-propenyl, $C_1$-$C_3$ alkyl, benzyl or substituted benzyl where the substitutents are one or two of the same or different and are selected from methyl, ethyl, methoxy, ethoxy, hydroxy, chloro, bromo, or fluoro;
$R^2$ is $C_2$-$C_3$ alkyl, allyl or cyclopropylmethyl;
$R^3$ and $R^4$ are both hydrogen or combine to form a carbon-carbon bond; and pharmaceutically acceptable acid addition salts thereof.

Preferred compounds of Formula I are those where:
X is CH;
Y is S;
$R^1$ is hydrogen or isopropyl;
$R^2$ is n-propyl;
$R^3$ and $R^4$ are both hydrogen; and pharmaceutically acceptable acid addition salts thereof.

Methods of preparing the compounds of Formula I and their precursors are taught in U.S. Pat. Nos. 4,166,182 and 4,675,322, and in Bach, et al., *J. Med. Chem.*, 23, 492–494 (1980) all of which are incorporated by reference herein in their entirety. Modifications to the above methods may be necessary to accommodate reactive functionalities of particular substituents. Such modifications would be both apparent, and known or readily ascertained, by those skilled in the art.

The pharmaceutically acceptable acid addition salts of the invention are typically formed by reacting a compound of Formula I with an equimolar or excess amount of acid. The reactants are generally combined in a mutual solvent such as diethyl ether or benzene, and the salt normally precipitates out of solution within about one hour to 10 days, and can be isolated by filtration or the solvent is stripped off by conventional means. Pharmaceutical formulations useful with compounds of Formula I are disclosed in U.S. Pat. No. 4,166,182.

The particular dosage of a compound of Formula I required to treat or inhibit bone demineralization according to this invention will depend upon the severity of the disease, its route of administration, and related factors that will be decided by the attending physician. Generally, accepted and effective doses will be from about 0.01 to about 10 mg, and more typically from about 0.1 to about 5 mg. Such dosages will be administered to a subject in need of treatment from once to about four times each day, or more often as needed to effectively inhibit the bone demineralization process.

As used herein, the term "inhibiting bone demineralization" should be understood as meaning preventing the decrease in bone mass with a static bone volume. This prevention may comprise a complete arresting of the demineralization process or a decrease in the progression of the demineralization process.

Pergolide was evaluated for inhibition of bone demineralization in the following test:

Pergolide, was added to a rat diet at the 0.001% by weight level. Groups of nine or ten rats, age three months, were put on the following diets, one group per diet: (1) a pergolide containing diet, ad libitum; (2) an L-DOPA containing diet ad libitum; and (3) pair fed, i.e., same feed consumption as pergolide-containing diet. After 18 months, although there were insufficient numbers of rats evaluated upon which to base statistically significant conclusions, pergolide appeared to be inhibiting bone demineralization; that is, there was higher bone density (g/cm$^2$) (obtained by dividing bone mineral content (g/cm) by bone width (cm)), between drug treated and the control group (Table 2). At 24 months, however, statistically significant differences were obtained, as set forth in Table 1. In Table 1, column 1 gives the diet; column 2, bone mineral content (BMC); column 3, bone width (BW); and column 4, bone density (BMC/BW), (column 2 divided by column 3).

TABLE 1

| Diet | BMC | BW | BMC/BW |
|---|---|---|---|
| Pair fed control | .07656 ± .00419 | .3770 ± .0088 | .2033 ± .0129 |
| .001% pergolide | .08733 ± .00100 | .3703 ± .0116 | .2368 ± .0346 |
| L-DOPA | .0822 ± .00691 | .3792 ± .0210 | .2173 ± .0215 |

Table 2 below gives the test results of the above evaluation conducted with pergolide where the measurements were made after 18 months of age. The data, particularly Table 1, establishes the ability of the ergot compound pergolide to inhibit bone demineralization.

TABLE 2

| Diet | BMC | BW | BMC/BW |
|---|---|---|---|
| Pair fed control | .08025 ± .00096 | .3745 ± .0075 | .2145 ± .0019 |
| .001% pergolide | .08700 ± .00572 | .3605 ± .0088 | .2415 ± .0195 |
| L-DOPA | .07900 ± .00424 | .3540 ± .0137 | .2235 ± .0095 |

It is apparent from the above data in Table 1 that rats on the pergolide-containing diet had statistically significant (95% confidence level or better) greater bone density than pairfed control rats.

Pergolide, was administered to the rats at a rate of 0.5 mg/kg of mammalian body weight. For a 50-100 kg human, the corresponding dose level would be about 25-50 mg/day. However, since humans are more sensitive to the pharmacologic actions of pergolide than are rats, dose levels in the range 0.1-10 mg of pergolide per day by the oral route would, in most instances, prevent, or a least slow the process of, bone demineralization, a universal part of the aging process in mammals.

The compound D-1-isopropyl-6-n-propyl-8β-methylthiomethyl ergoline was evaluated for its ability to inhibit bone demineralization in an ovariectomized rat model according to the following procedures. Briefly, this model uses ovariectomized rats which show a significant degree of trabecular bone loss at four weeks following the removal of the ovaries. Typically, β-estradiol will completely protect the bones from the ovariectomy-induced lesion.

Animals. Seventy-five day old, female Sprague Dawley rats (weight range of 225 to 275 g; Charles River, Portage, MI) were used in these studies. Ovariectomies (or a sham surgical procedure for controls) were performed by the vendor. The animals were shipped one week post-surgery and housed in hanging wire cages in groups of four. Room temperature was maintained at 22.2°±1.7° C. with a minimum relative humidity of 40%. The photoperiod in the room was 12 hours light and 12 hours dark, with light onset at 0600 hour. The animals had ad lib access to food (Teklad diet, TD 89222, 0.5% calcium, 0.4% phosphorous; Madison, WI) and water. The animals were allowed one week to acclimate to these conditions prior to experimental manipulation.

Materials. Suspensions of D-1-isopropyl-6-n-propyl-8β-methylthiomethyl ergoline as the hydrochoride salt were prepared in 1% carboxymethylcellulose (CMC). One percent CMC injections were used as the control vehicle. β-Estradiol (obtained from Sigma Chemical Co.; St. Louis, MO) was suspended in a 20% polyethylene glycol vehicle and was employed as an internal standard for these studies.

Protocol. At the end of the one week acclimatization period (therefore, two weeks post-ovariectomy), dosing with test compounds was initiated. Subcutaneous injections of 1% CMC, D-1-isopropyl-6-n-propyl-8β-methylthiomethyl ergoline (0.1 to 3 mg/kg) or β-estradiol (100 μg/kg) were delivered daily for two consecutive weeks. On the day following the fourteenth dose (four weeks post-ovariectomy), the animals were asphyxiated with carbon dioxide, body weight and uterine weight were recorded, and the left femur was removed and frozen ($-20°$ C.).

Bone Assays. Single photon absorptiometry was performed on the left femur using a Norland 2780 x-ray densitomer. Triplicate readings were made at the proximal aspect of the patellar groove. Bone mineral density was calculated as a function of the bone mineral content and bone width at the point of measurement.

Statistics. Each experimental group consisted of 8-16 animals. Data for control and treated rats were compared by one way analysis of variance (ANOVA). When statistical significance was indicated ($p<0.05$) post-hoc range testing was performed (Scheffe F test).

TABLE 3

| Group | Bone Mineral Density[a] |
|---|---|
| Control | 100.0 ± 7.6 |
| Ovariectomy | 0.6 ± 5.3 |
| β-Estradiol (100 μg/kg) | 70.8 ± 8.8[b] |
| 0.01 mg/kg | 29.2 ± 10.7 |
| 0.03 mg/kg | 37.8 ± 7.3[b] |
| 0.1 mg/kg | 37.9 ± 5.6[b] |
| 0.3 mg/kg | 50.3 ± 3.7[b] |
| 1.0 mg/kg | 53.4 ± 8.6[b] |
| 3.0 mg/kg | 47.8 ± 6.7[b] |

[a]Bone mineral density values are presented as percent protection (± Standard Error of Mean (SEM) from loss induced four weeks after ovariectomy. % protection = [($bmc_{test} - bmc_{ovx}$)/($bmc_{control} - bmc_{ovx}$)] × 100
[b]$p < 0.05$ vs. ovariectomy group It is advantageous to administer a compound of Formula I by the oral route to an aging mammal (e.g., a post-menopausal female) mammal or to any aging male showing evidence of bone demineralization by x-ray. For such purposes, the following oral dosage forms are available. "Active ingredient" means a compound of Formula I.

Hard gelatin capsules are prepared using the following ingredients:

| | Quantity (mg/capsule) |
|---|---|
| Active ingredient | 0.01-10 mg |
| Starch dried | 200 |
| Magnesium stearate | 10 |

The above ingredients are mixed and filled into hard gelatin capsules.

A table formulation is prepared using the ingredients below:

| | Quantity (mg/capsule) |
|---|---|
| Active ingredient | 0.01-10 mg |
| Cellulose, microcrystalline | 400 |
| Silicon dioxide, fumed | 10 |
| Stearate acid | 5 |

The components are blended and compressed to form tablets.

Alternatively, tablets each containing 0.1-10 mg of active ingredient are made up as follows:

| Active ingredient | 0.01-10 mg |
|---|---|
| Starch | 45 mg |
| Microcyrstalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules each containing 0.01-10 mg of medicament are made as follows:

| Active ingredient | 0.01-10 mg |
|---|---|
| Starch | 59 mg |
| Microcyrstalline cellulose | 59 mg |
| Magnesium stearate | |

The active ingredient, cellulose, starch, and magnesium stearate are blended, passed through a No. 45 mesh U.S. sieve, and filled into hard gelatin capsules.

Suspensions each containing 0.01-10 mg of medicament per 5 ml dose are made as follows:

| Active ingredient | 0.01-10 mg |
|---|---|
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor, and color are diluted with some of the water and added, with stirring. Sufficient water is then added to produce the required volume.

It should be understood that the instant specification and examples are set forth by way of illustration and not limitation, and that various modifications and changes may be made without departing from the spirit and scope of the present invention as defined by the appended claims.

We claim:

1. A method of inhibiting bone demineralization comprising administering to a mammal in need of treatment an effective amount of a compound having the formula

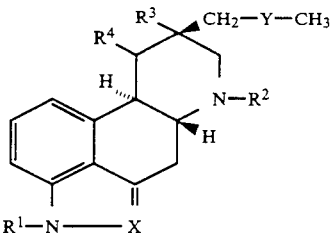

where
X is CH or N;
Y is O or S;
$R^1$ is 2-propenyl, $C_1$-$C_3$ alkyl, benzyl or substituted benzyl where the substitutents are one or two of the same or different and are selected from methyl, ethyl, methoxy, ethoxy, hydroxy, chloro, bromo, or fluoro;
$R^2$ is $C_2$-$C_3$ alkyl, allyl or cyclopropylmethyl;
$R^3$ and $R^4$ are both hydrogen or combine to form a carbon-carbon bond; and pharmaceutically acceptable acid addition salts thereof.

2. A method according to claim 1 where
X is CH;
Y is S;
$R^1$ is hydrogen or isopropyl;
$R^2$ is n-propyl; $R^3$ and $R^4$ are both hydrogen, and pharmaceutically acceptable acid addition salts thereof.

3. A method according to claim 2 in which the mammal has been diagnosed as suffering from osteoporosis.

4. A method according to claim 3 in which the mammal is a post-menopausal female mammal.

5. A method according to claim 3 in which the dose is 0.01 to 10 mg/day.

6. A method according to claim 2 where said compound is pergolide or a pharmaceutically acceptable acid addition salt thereof.

7. A method according to claim 2 where said compound is D-1-isopropyl-6-n-propyl-8β-methylthiomethyl ergoline or a pharmaceutically acceptable acid addition salt thereof.

* * * * *

UNITED STATES PATENT AND TRADEMARK OFFICE
CERTIFICATE OF CORRECTION

PATENT NO. : 5,063,234

DATED : November 5, 1991

INVENTOR(S) : Henry U. Bryant and James A. Clemens

It is certified that error appears in the above-identified patent and that said Letters Patent is hereby corrected as shown below:

Column 3, line 66, that portion of the definition of $R^1$ which reads "2-propenyl, $C_1$-$C_3$ alkyl, benzyl or substituted" should read --hydrogen, 2-propenyl, $C_1$-$C_3$ alkyl, benzyl or substituted--.

Claim 1, line 8 (at column 8, line 24) that portion of the definition of $R^1$ which reads "2-propenyl, $C_1$-$C_3$ alkyl, benzyl or substituted" should read --hydrogen, 2-propenyl, $C_1$-$C_3$ alkyl, benzyl or substituted--.

Signed and Sealed this

Sixth Day of April, 1993

Attest:

STEPHEN G. KUNIN

*Attesting Officer*     *Acting Commissioner of Patents and Trademarks*